US007006872B2

(12) United States Patent
Gielen et al.

(10) Patent No.: US 7,006,872 B2
(45) Date of Patent: Feb. 28, 2006

(54) CLOSED LOOP NEUROMODULATION FOR SUPPRESSION OF EPILEPTIC ACTIVITY

(75) Inventors: Frans L. H. Gielen, Eckelrade (NL); Wytse J. Wadman, Bussum (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/388,926

(22) Filed: Mar. 13, 2003

(65) Prior Publication Data
US 2003/0181955 A1 Sep. 25, 2003

Related U.S. Application Data

(63) Continuation of application No. 09/842,813, filed on Apr. 27, 2001, now Pat. No. 6,671,555.

(51) Int. Cl.
*A61B 5/0484* (2006.01)
*A61N 1/18* (2006.01)
(52) U.S. Cl. .......................................... 607/45; 600/544
(58) Field of Classification Search ................ 607/45, 607/66, 72; 600/544, 554
See application file for complete search history.

(56) References Cited

U.S. PATENT DOCUMENTS

| | | | |
|---|---|---|---|
| 4,867,164 A | | 9/1989 | Zabara .......................... 607/45 |
| 5,025,807 A | | 6/1991 | Zabara .......................... 607/45 |
| 5,263,488 A | * | 11/1993 | Van Veen et al. ............. 600/544 |
| 5,392,788 A | * | 2/1995 | Hudspeth ..................... 600/544 |
| 5,713,923 A | | 2/1998 | Ward et al. ...................... 607/3 |
| 5,938,688 A | * | 8/1999 | Schiff ........................... 607/45 |
| 5,941,906 A | * | 8/1999 | Barreras, Sr. et al. ......... 607/66 |
| 6,018,682 A | | 1/2000 | Rise .............................. 607/45 |
| 6,128,538 A | | 10/2000 | Fischell et al. ................ 607/45 |
| 6,224,549 B1 | * | 5/2001 | Drongelen ................... 600/300 |
| 6,459,936 B1 | | 10/2002 | Fischell et al. ................ 607/45 |
| 6,463,328 B1 | * | 10/2002 | John ............................. 607/45 |
| 6,466,822 B1 | | 10/2002 | Pless ............................ 607/45 |
| 6,539,263 B1 | * | 3/2003 | Schiff et al. ................... 607/45 |
| 6,591,138 B1 | * | 7/2003 | Fischell et al. ................ 607/45 |
| 6,597,594 B1 | * | 7/2003 | Waller .......................... 365/49 |
| 2002/0072770 A1 | | 6/2002 | Pless ............................. 607/2 |

OTHER PUBLICATIONS

Lead Kit for Brain Stimulation (Parkinson's Disease), Lead Implant Manual 3387.
Lead Kit for Deep Brain Stimulation, Leads Models 3387, 3389.
Physician and Hospital Staff Manual, Model 7428 Neurostimulator.
F.H. Lopes da Silva et al., "Dynamics of Local Neuronal Networks: Control Parameters and State Bifurcates in Epileptogenesis", *Progress in Brain Research*, 1994, vol. 102, pp. 359-370, Amsterdam, The Netherlands.
Ivan Osorio et al., "Real-Time Automated Detection and Quantitative Analysis of Seizure and Short-Term Prediction of Clinical Onset", *Epilepsia*, Jun. 1998, vol. 39, No. 6, pp. 615-627.

(Continued)

*Primary Examiner*—Carl Layno
(74) *Attorney, Agent, or Firm*—John W. Albrecht

(57) ABSTRACT

A system and method for predicting the likelihood of occurrence of an impending neurological episode. Electrical stimuli are delivered to a structure of the brain. Response field potentials evoked by the stimuli are sensed. Analysis of these field potentials allows for predictions as to the occurrence of an impending, but not yet occurring, neurological disorder. In one example, a measurement of change in response pulses is used to determine a level of interconnectivity in the structures of the brain. The level of functional interconnectivity is used in predicting the occurrence of the neurological event. An example of such a neurological event includes an epileptic seizure.

101 Claims, 8 Drawing Sheets

OTHER PUBLICATIONS

Hao Qu et al., "A Patient-Specific Algorithm for the Detection of Seizure Onset in Long-Term EEG Monitoring: Possible Use as a Warning Device", *IEEE Transactions on Biomedical Engineering*, Feb. 1, 1997, vol. 44, No. 2, pp. 115-122, IEEE Inc., New York.

Marcos Velasco et al., "Acute and Chronic Electrical Stimulation of the Centromedian Thalamic Nucleus: Modulation of Reticulo-Cortical Systems and Predictor Factors for Generalized Seizure Control", *Elsevier, Archives of Medical Research*, 2000, No. 31, pp. 304-315.

C.L. Wilson et al., "Paired Pulse Suppression and Facilitation in Human Epileptogenic Hippocampal Formation", *Epilepsy Research*, Aug. 1998, vol. 31, No. 3, pp. 211-230.

* cited by examiner

CLOSED LOOP NEUROMODULATION FOR SUPPRESSION OF EPILEPTIC ACTIVITY

CROSS REFERENCE TO RELATED APPLICATION

This application is a continuation of application Ser. No. 09/842,813 filed Apr. 27, 2001 now U.S. Pat. No. 6,671,555 which is hereby incorporated by reference.

FIELD OF THE INVENTION

This invention relates to the treatment of neurological disorders, and more particularly techniques for the treatment of epileptic seizures.

BACKGROUND OF THE INVENTION

Epilepsy is a condition characterized by recurrent seizures, which are the outward manifestation of excessive and/or hyper-synchronous abnormal electrical activity of neuronal structures of the brain. A seizure occurs when the electrical activity of brain structures or even the whole brain becomes abnormally "synchronized." This is the operational definition of an epileptic seizure.

A seizure patient may suffer from any combination of different types of seizures. Grand mal seizures are the most common form of epilepsy and are characterized by convulsions with tonic-clonic contractions of the muscles. Absence seizures (previously referred to as "petit mal") are characterized by a brief and sudden loss of consciousness. The psychomotor form of seizures is characterized by a clouding of consciousness for one or two minutes. A complex partial seizure is characterized by a complete loss of consciousness. The type of seizure experienced is typically dependent upon the portion of the cerebral cortex where hypersynchronous activity is occurring. Many types of seizures generally involve the entire brain, while certain types, such as partial seizures, begin in one part of the brain and may remain local.

Regardless of the type of epilepsy, seizures significantly limit the autonomy of the patient. When hit with a seizure, the patient typically loses some level of control of his/her body. In most cases, seizures occur without prior warning to the patient. As a result, epileptic seizures pose a serious safety hazard to the patient and others surrounding the patient. For example, a patient hit with a sudden seizure while driving a car may endanger the patient's own safety as well as the safety of others. Seizure patients are also exposed to a risk of bodily harm when operating machinery and even in daily activities such as crossing a street or going down stairs. In addition to this safety hazard, each seizure will further damage brain structures often resulting in progressive loss of brain function over time.

Researchers have developed a number of techniques for treating seizure disorders and its symptoms. For example, research has shown that inhibiting (namely, reducing the excitation of neurons) the substantia nigra in the brain increases the threshold for seizure occurrence. Researchers have also found that increasing the activity of neurons in the external Globus Pallidum (GPe) increases inhibition of neurons in the subthalamic nucleus, which in turn inhibits neural activity in the substantia nigra.

Neurosurgeons have also been able to diminish the symptoms of many neural disorders by lesioning certain brain areas. Examples include lesioning the ventral lateral portion of the internal Globus Pallidus and the Vim Thalamus for treating movement disorders. Electrical stimulation of the nervous system has also been used to suppress seizures. Finally, infusion of certain drugs into a region of the brain can affect the excitability of the neurons at the site of infusion as disclosed in U.S. Pat. No. 5,713,923 (Ward et al.) assigned to Medtronic, Inc.

Others have studied the effects of electrically stimulating the vagus nerve as a means of suppressing epileptic activity. It has been observed that stimulation of the vagus nerve with certain parameters caused de-synchronization of the brain's electrical activity in animal models. These concepts were disclosed by Zabara in U.S. Pat. Nos. 4,867,164 and 5,025,807.

Under another approach, researchers have devised algorithms to detect the onset of a seizure. Qu and Gotman reported a system that recognizes patterns of electrical activity similar to a template developed from recording an actual seizure. See H. Qu and J. Gotman, "A Seizure Warning System for Long-term Epilepsy Monitoring", Neurology, 1995;45:2250–2254. Also, see I. Osario, M. Frei, D. Lerner, S. Wilkinson, "A Method for Accurate Automated Real-time Seizure Detection", Epilepsia, Vol. 36, Suppl. 4, 1995. In each of these techniques for recognizing the onset of a seizure, the developers employ two processes. The first process is to extract certain features from the signals representing the electrical activity of the brain. Examples of the signal features include the signal power or the frequency spectrum of the signals. The second process is to recognize a pattern or set of values for those features that characterize a brain state that will reliably lead to a seizure.

Using pattern recognition techniques, closed-looped protocols for responding to the onset of an epileptic seizure have also been suggested. For example, U.S. Pat. Nos. 6,128,538 and 6,134,474 report closed-loop systems for identifying and responding to a neurological disease, such as epilepsy. These systems, however, identify and respond to neurological events that have already begun. Once started, these events may be difficult to correct. Therefore, a need for more efficient and effective treatments of neurological events continues to exist. Table 1 lists documents that disclose systems and methods that provide for seizure detection.

TABLE 1

| U.S. Pat. No. | Inventors | Title |
| --- | --- | --- |
| 4,867,164 | Zabara | Neurocybernetic prosthesis |
| 5,025,807 | Zabara | Neurocybernetic prosthesis |
| 5,713,923 | Ward et al. | Techniques for treating epilepsy by brain stimulation and drug infusion |
| 6,128,538 | Fischell et al. | Means and method for the treatment of neurological disorders |
| 6,134,474 | Fischell et al. | Responsive implantable system for the treatment of neurological disorders |
| | | H. Qu and J. Gotman, "A Seizure Warning System for Long-term Epilepsy Monitoring", Neurology, 1995; 45: 2250–2254 |
| | | I. Osario, M. Frei, D. Lerner, S. Wilkinson, "A Method for Accurate Automated Real-time Seizure Detection", Epilepsia, Vol. 36, Suppl. 4, 1995. |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to the treatment of neurological disorders, and with respect to the treatment of epileptic seizures in particular. Such problems include, for example, treating neurological events only after they have started and, in particular, treating epileptic seizures only after they have started, the present inability to predict the likelihood of the occurrence of an impending neurological event, the present inability to predict the likelihood of the occurrence of an impending epileptic seizure, the present inability to provide therapy to a patient in order to avert the onset of an impending, but not yet started, neurological event, and the present inability to provide therapy to a patient in order to avert the onset of an imminent, but not yet started, epileptic seizure. Various embodiments of the present invention have the object of solving at least one of the foregoing problems.

It is an object of the present invention to overcome at least some of the disadvantages of the foregoing systems by providing a system and method that probe the excitable state of the brain or a specific sub region of the brain and relate a measurement acquired via the probe to the likelihood of the occurrence of an impending neurological event.

It is a further object of the invention to provide a method of signal analysis to predict the likelihood of the occurrence of a neurological disorder or event prior to the start of the event and to provide therapy to the brain when a neurological disorder and/or event is predicted.

In addition, it is an object of the invention to provide an implantable system for delivering electrical stimuli to and analyzing response field potentials from the brain to predict the likelihood of the occurrence of a neurological disorder and/or event prior to the start of the event.

It is another object of the invention to provide a system and method of signal analysis to predict the likelihood of the occurrence of an impending epileptic seizure.

It is an object of the invention to determine a level of functional interconnectivity in brain structures and to use the level in the prediction of impending neurological disorders.

Various embodiments of the invention may possess one or more features capable of fulfilling the above objects. Instead of sensing and responding to a neurological event that has already begun, the present invention involves sensing and responding to precursors of an impending neurological event. Therapy can then be delivered to avert the onset of the neurological event. Therapy to prevent an impending neurological event may be less traumatic for the patient and less demanding on system resources, e.g., battery energy levels, for treating the event.

Some embodiments of the invention include one or more of the following features: one or more electrodes implantable in a structure of a brain and a signal processor/generator coupled to the electrodes; the signal generator including an electrical pulse generator to deliver electrical stimuli to the brain via the electrodes implanted in the structure of the brain; the signal generator including a signal analyzer to receive via the electrodes response field potentials to the electrical stimuli delivered with the electrical pulse generator; the signal analyzer receiving response field potentials through the electrodes and predicting the likelihood of the occurrence of a neurological disorder based on the sensed response field potentials.

The invention involves predicting the likelihood of occurrence of neurological disorders within the brain by chronically measuring and analyzing the excitable state of the brain in terms of a balance between the levels of excitation and levels of inhibition in certain parts of the brain evoked by electrical stimuli given to brain structures. The structures instrumental in this balance may or may not be the brain structures that are directly involved with the onset of the neurological disorder within the brain. Nevertheless, the balance between excitation and inhibition is used as an indicator of the likelihood that a neurological disorder, such as a seizure, is about to occur.

In one embodiment, the present invention provides for electrical stimuli to be delivered to a structure of the brain. Response field potentials to the stimuli are sensed and analyzed to predict the occurrence of a neurological disorder. In an alternative embodiment, response magnetic fields, and their respective vectors, are measured and analyzed to predict the occurrence of the neurological disorder. An example of such a disorder is an epileptic seizure.

Short electrical stimuli are delivered to the brain region under investigation. These stimuli will activate the nerve fibers that naturally activate the brain structures. Activity of the nerve cells is accompanied by an electrical field in their immediate surrounding, the local field potential, which can be measured with indwelling electrodes and under the right circumstances used to deduce the cellular activity. Alternatively, the activity of the nerve cell is accompanied by a magnetic field in their immediate surrounding, the local magnetic field potential and associated vectors, are used to deduce the cellular activity. In the present invention, single electrical stimuli can be used. However, more complex spatially and temporally organized sets of stimuli can be used in order to test the excitable state of the local neuronal circuit.

Using combinations of well timed stimuli will bring the structure in highly specific states of excitability and allow to extract among other aspects the balance between excitation and inhibition. The typical and most simple example is to give two successive stimuli, the first one puts the region into an excitable state (which can be measured) such that the second can then be used to measure the relative level of inhibition.

The electrical stimuli delivered to the brain can include pairs of two or more electrical stimuli. For example, such a pulse pattern can include a repetitively delivered pair of stimuli having a first stimulus and a second stimulus. The response field potentials of the brain to the first and second stimuli are sensed and measurements of change in the responses made. The change in the response field potentials is used to determine a level of functional interconnectivity in structures of the brain affected by the given stimuli. In an alternative embodiment, response magnetic fields, and their respective vectors, are measured and analyzed to determine the level of functional interconnectivity in structures of the brains affected by the given stimuli.

The level of functional interconnectivity can be determined by calculating a ratio of the response field potentials, or response magnetic fields, resulting from the pairs of first and second stimuli. A plot of the ratio indicates the level of functional interconnectivity in structures of the brain influenced by the stimuli. Features from the plot of the ratio may indicate when a neurological event is imminent. For example, possible features from the plot include, but are not limited to, rising (positive) or falling (negative) slope of the response, under or overshoot, time to peak, half width of the response, description of the response with an alfa-function, or a series of exponential functions raised to any order. When these features are identified, therapy can be delivered to treat the impending neurological event. Both the sensing and therapeutic aspects of the invention can be embodied or delivered via an implantable device that is carried by the patient for continuous use.

In comparison to known implementations of detecting and treating neurological disorders, various embodiments of the present invention may provide one or more of the following advantages: probing the excitable state of the brain or a specific sub region of the brain and relating a measurement acquired via the probe to the likelihood of the occurrence of an impending neurological event; predicting the likelihood of the occurrence of an impending neurological event prior to the start of the event; providing therapy to the brain when a neurological disorder and/or event is predicted; and predicting the likelihood of the occurrence of an impending epileptic seizure.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DESCRIPTION OF THE PREFERRED EMBODIMENTS

Figure 1:
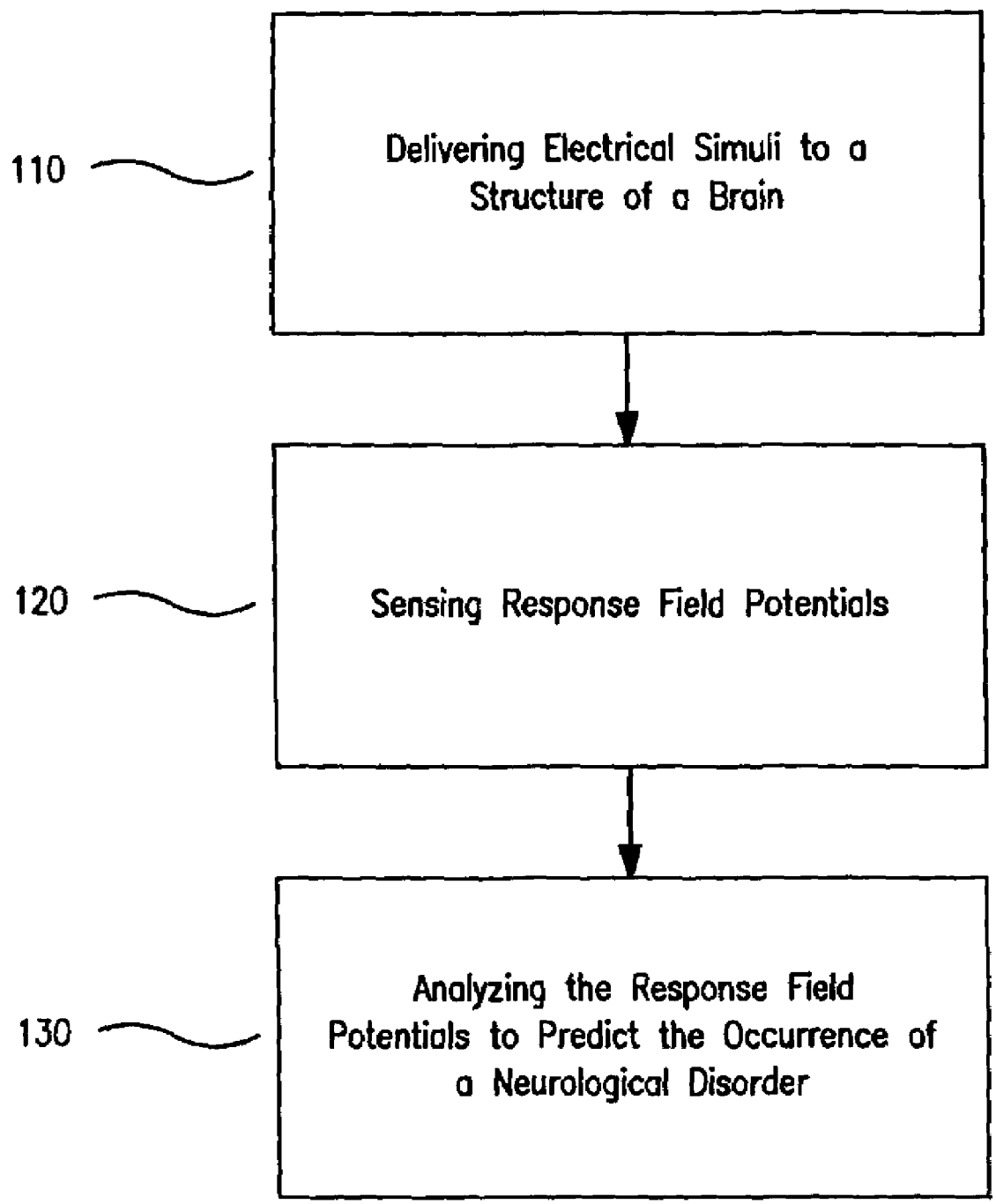
FIG. 1 is a flow chart illustrating a technique for predicting the occurrence of a neurological disorder in accordance with the present invention.

The present invention involves techniques for analyzing sensed response field potentials, or sensed magnetic fields, to predict the likelihood of occurrence of a neurological event. In one embodiment, the prediction is based on measurements and analysis of a balance between the level of excitation and the level of inhibition in a brain structure. The balance can be envisioned as a measure of local excitability of the brain structure. Features from this measure of local excitability, in turn, correlate strongly with impending, but not yet occurring, neurological events. In one embodiment, the present invention is particularly useful in predicting the onset of an epileptic seizure.

Brain cells are capable of generating influences on other brain cells. These influences include excitatory influences and inhibitory influences. Each brain cell has a large number of excitatory and inhibitory inputs from many different brain cells. Each cell adds these excitatory and inhibitory inputs together. The sum of the excitatory and inhibitory inputs causes either increased or decreased activity in the cell. When a threshold level of excitatory influences is achieved, e.g., the balance of excitatory and inhibitory signals shifts towards excitatory, the cell produces an action potential that transports excitatory and/or inhibitory information to connecting brain cells. Thus, the activity level in each cell influences the activity level, i.e., excitatory or inhibitory, of a connecting brain cell. This influence of each brain cell to connecting brain cells can, therefore, be thought of as a balance between the excitatory or inhibitory influences on the brain cells.

The present invention measures changes in the balance between the excitatory or inhibitory influences on the brain cells. This information is then used to assess and predict the likelihood of occurrence of a neurological event. To acquire this informnation, electrical stimuli are introduced into a brain structure. In one embodiment, response field potentials to the introduced electrical stimuli are sensed and analyzed. Alternatively, response magnetic fields are sensed and analyzed. The magnitude of the response field potentials, or the magnitude of the response magnetic fields, provides an indication of the balance in the brain cells involved in transferring the electrical signals introduced into the brain structure. This induced effect reflects the functional interconnectivity between the brain structure where the electrical stimuli are introduced and the brain structures where the response field potentials, or response magnetic field potentials, are sensed.

Conventional epilepsy predicting procedures determine whether a sensed Electroencephalogram (EEG) starts to show synchrony as opposed to the normal stochastic features. Thus, the seizure is identified only after it has started. In contrast, the present invention uses the functional interconnectivity measurements of the brain structures to identify the likelihood of the occurrence of an impending, but not yet started, epileptic seizure. As a result, the present invention enables therapy to be provided to the brain in order to remove the cause or moderate the impending epileptic seizure. It is believed that removing the cause of the seizure in this way is much easier than stopping an already existing seizure.

While many of the examples presented below are directed to the detection and treatment of an epileptic seizure, it is recognized that the present invention is not limited only to the detection and treatment of epileptic seizures. For example, the present invention can be used to predict and treat any number of conditions within the brain. Examples of these conditions include, but are not limited to, migraine headaches, Parkinson's disease, schizophrenia, depression, mania, or other neurological disorders where changes in the balance of the excitatory or inhibitory influences on the brain cells may provide indications of an impending pathological event.

FIG. 1 is a flow diagram illustrating a method according to one embodiment of the present invention. At 110, electrical stimuli are delivered to a brain structure. In one embodiment, the brain structures for delivering the stimuli include, but are not limited to, an afferent fiber and/or efferent fiber system in the sub thalamic nucleus, the hippocampus, the medial thalamus and/or the temporal lobe of the brain. However, because neurological disorders, such as epilepsy, can be generated in a wide variety of brain structures, the exact location to which the electrical stimuli are delivered may need to be determined for each individual case.

The electrical stimuli are delivered in a pulse pattern to the brain structure. The pulse pattern of electrical stimuli can include pairs of two or more electrical stimuli delivered to the brain structure. Alternatively, the pulse pattern of electrical stimuli can be a short train, or burst, of a predetermined number of stimuli. The exact pattern and number of electrical stimuli in the pulse pattern is selected based in part on the brain structure to which the stimuli are delivered. In one embodiment, the pulse pattern is repeated such that the electrical stimuli are continuously delivered to the patient.

In one embodiment of the present invention, the pulse pattern is a pair of stimuli to the brain structure. In this example, the pair of stimuli includes a first and a second stimulus, where the stimuli are separated by a predetermined time interval. In one embodiment, the predetermined time interval is a programmable value of 21 milliseconds, but this interval may range from 5 to 100 milliseconds. In an additional embodiment of the present invention, the predetermined time interval is a programmable value having a range from 5 to 2000 milliseconds, 10 to 2000 milliseconds, 20 to 2000 milliseconds, 40 to 2000 milliseconds, 100 to 2000 milliseconds, 1000 to 2000 milliseconds, 5 to 1000 milliseconds, 10 to 1000 milliseconds, 20 to 1000 milliseconds, 40 to 1000 milliseconds, 100 to 1000 milliseconds, 10 to 100 milliseconds, 20 to 100 milliseconds, 40 to 100 milliseconds, 5 to 10 milliseconds, 5 to 20 milliseconds, 5 to 40 milliseconds, 10 to 20 milliseconds, 10 to 40 milliseconds, or 20 to 40 milliseconds. The specific time interval used depends upon the brain structure being analyzed for functional interconnectivity.

Additional electrical stimulus parameters are also programmable. Exact parameter values are specific for the brain structure involved. For example, the duration of each stimulus can be programmed in a range of 30 microseconds to 10 milliseconds, 30 microseconds to 1 millisecond, 30 microseconds to 0.1 milliseconds, 100 microseconds to 10 milliseconds, 100 microseconds to 1 milliseconds, or 1 millisecond to 10 milliseconds. The typical duration of pulses ranges between about 30 microseconds and about 10 milliseconds. Additionally, the waveform shape of the stimuli can also be programmed. Waveform shapes can include, but are not limited to, rectangular, sinusoidal and/or ramped signals. Other known waveform shapes can also be useful.

The amplitude or magnitude of the stimulation signals provided in accordance with the present invention, such as, by way of example, amplitude or magnitude of the stimulus of the first pulse pattern, is also a programmable value generally ranging between about 10 microamperes and about 10 milliamperes. Other ranges of magnitudes or amplitudes of stimulation signals are also possible, of course, such as between about 10 microamperes to about 10 mA, between about 20 microamperes and about 5 mA, between about 40 microamperes and about 2.5 mA, between about 50 microamperes and about 2 mA, and between about 100 microamperes and about 2 mA (which is the typical range amplitude or magnitude values for electrical stimulation of the human brain in accordance with at least one embodiment of the present invention). At signal amplitudes or magnitudes exceeding about 10 microamperes there exists the danger of harming brain tissue. Such a limit may also be expressed in terms of current density, or electrical charge per phase. The practical limit for electrical stimulation of the brain in accordance with the present invention is about 20 microCoulombs per phase. Although the stimulation signals provided in the present invention may assume different forms such as square waves, rectangular waves, ramping waves, swept or chirp signals, or sinusoidal waves, for example, it is desired that for chronic stimulation the total charge delivered by an implantable lead disposed within the human brain be charge balanced over each waveform cycle or period so as to prevent tissue damage from occurring as a result of charge imbalances.

The pulse pattern of electrical stimuli is typically delivered two or more times. In one embodiment, the pulse pattern is repeatedly delivered to the patient in order to monitor the patient for an impending neurological event. The repeated delivery of the pulse pattern includes a repetition frequency, where the repetition frequency is programmed in the range of 1 second to 30 minutes, 10 seconds to 30 minutes, 30 seconds to 30 minutes, 1 minute to 30 minutes, 5 minutes to 30 minutes, 10 minutes to 30 minutes, 20 minutes to 30 minutes, 1 second to 20 minutes, 10 seconds to 20 minutes, 30 seconds to 20 minutes, 1 minute to 20 minutes, 5 minutes to 20 minutes, 10 minutes to 20 minutes, 1 second to 10 minutes, 10 seconds to 10 minutes, 30 seconds to 10 minutes, 1 minute to 10 minutes, 5 minutes to 10 minutes, 1 second to 5 minutes, 10 seconds to 5 minutes, 30 seconds to 5 minutes, 1 minute to 5 minutes, 1 second to 1 minute, 10 seconds to 1 minute, 30 seconds to 1 minute, 1 second to 30 seconds, 10 seconds to 30 seconds, 1 second to 10 seconds, 10 milliseconds to 5 seconds, and 100 milliseconds to 1 second. Of course, other values are also possible.

One existing deep brain stimulation (DBS) lead adaptable for use in the present invention is the Medtronic Model No. 3387 ACTIVA DBS lead. Such leads feature stimulation electrodes having relatively small surface areas of around 6 square millimeters, and thus relatively high impedances of around 1 kOhm. Stimulation electrodes having surface areas ranging between about 0.1 square millimeters to about 1 square millimeter represent the lower practical limit for stimulation electrode surface area in the present invention, for at electrode surface areas less than these current densities become too high and can result in damage to human brain tissue. At the other end of the scale electrode surface areas exceeding about 15 square millimeters represent an upper practical limit because the corresponding impedances of such large surface area electrodes (e.g., around 200 to 500 Ohms) become too low. Preferred ranges for electrode surface areas in the present invention are between about 1 square millimeter and about 6 square millimeters, with corresponding respective impedances of about 1 kOhm, and about 6 kOhms. Preferred materials for forming the electrodes include, but are limited to, platinum/iridium alloys and mixtures.

Applicants hereby incorporate by reference herein, each in its respective entirety, the following printed publications: (1) Physician and Hospital Staff Manual for MEDTRONIC KINETRA Dual Chamber Neurostimulator for Deep Brain Stimulation, Model 7428 Neurostimulator, Part Number 197583-001; (2) MEDTRONIC Lead Implant Manual for Model Number 3387, Copyright 1994, MEDTRONIC B. V.;

(3) MEDTRONIC DBS Technical Manual for Lead Models 3387 and 3389, UC9402608ML/196984-017 Revision A, 1998.

The present invention includes within its scope not only electrically stimulating human brain tissue in a certain fashion, but also sensing electrical and magnetic signals originating in the human brain. In the respect of sensing or detecting such signals, in the present invention it is contemplated that signals ranging between about 10 microVolts and about 10 milliVolts, and between about 500 microVolts and about 5 millivolts be sensed. The amplitude or magnitude of the signal(s) to be sensed depends at least in part upon the size of the brain structure which generates signals of interest. The larger such a brain structure is, the greater the amplitude or magnitude of the corresponding signal to be sensed.

Additionally, electrical stimulation signals and/or sensed electrical or magnetic signals may be delivered or detecting using one or more electrodes and/or arrays of electrodes. Stimulation and sensing electrodes of the present invention may also assume a variety of different shapes and configurations, such as round electrodes, "windowed" electrodes, spirally wound electrodes, flat electrodes, circular electrodes and so on. Stimulation signals of the present invention may be beamed or directed in certain directions towards desired portions of the brain through various means such as employing weighted arrays of electrodes, turning certain stimulation electrodes on which face in a first direction while turning off other electrodes which face in a direction different from the first direction, and so on. Similarly, arrays of electrodes or multiple electrodes may be employed to more accurately sense and determine the point or region of origin of certain electrical or magnetic signals generated within the human brain.

Referring to FIG. 1 again, at 120 response field potentials to the electrical stimuli delivered to the brain structure are sensed. In one embodiment, these response field potentials are sensed from within the same brain structure where the electrical stimuli were delivered, or at least to where the fibers activated by the stimuli project and make contact. For example, one or more of the same or additional electrodes, discussed in detail below, are used to sense the response electrical potentials. Alternatively, electrodes implanted in a brain structure separate from the brain structure where the electrical stimuli were delivered are used to sense the response electrical potentials to elsewhere delivered stimuli. Examples of two brain structures where the electrodes can be located include an identified epileptogenic brain structures and a non-epileptogenic brain structure. One example of a common epileptogenic brain structure is the hippocampus.

In an alternative embodiment, response magnetic fields, including their respective vectors, to the electrical stimuli delivered to the brain structure are sensed. These response magnetic fields can be sensed from within the same brain structure where the electrical stimuli were delivered, or at least to where the fibers activated by the stimuli project and make contact. For example, one or more of the same or additional electrodes, discussed in detail below, are used to sense the response magnetic fields. Alternatively, electrodes implanted in a brain structure separate from the brain structure where the electrical stimuli were delivered are used to sense the response magnetic fields to elsewhere delivered stimuli.

As discussed, the pulse pattern delivered to the brain structure can include pairs of stimuli (e.g., first and second stimuli). One important aspect of sensing the response field potentials, or the response magnetic fields, to these stimuli pairs is measuring any changes that occur in the responses to the second stimulus as compared to the response to the first stimulus. In one embodiment, measuring the change in the response field potentials is accomplished by measuring the field potentials of the response to the first stimuli and the field potentials of the response to the second stimuli. The differences in the field potentials evoked by the first and second stimuli are then used to determine the state of functional interconnectivity of monitored structures within the brain. In an alternative embodiment, measuring the change in the response magnetic fields is accomplished by measuring the magnetic field of the response to the first stimuli and the magnetic field of the response to the second stimuli. The differences in the magnetic fields evoked by the first and second stimuli are then used to determine the state of functional interconnectivity of monitored structures within the brain.

One way of determining the functional interconnectivity of the brain structures is to take a ratio of the magnitude of field potentials, or magnetic fields, evoked by the first stimulus and the second stimulus. Other relevant measurements of the field potentials and/or magnetic fields might also be used. In one embodiment, the ratio is between the response field potentials, or magnetic fields, evoked by the first stimuli, P1, and the response field potentials evoked by the second stimuli, P2. The variations in the ratio, P1/P2, over time are then analyzed as they may represent the functional interconnectivity of the brain structures. In one embodiment, particular variations, or trends, in the slope of the ratio are taken as indicators of an impending neurological event.

At 130 of FIG. 1, the sensed response field potentials are analyzed to predict the likelihood of occurrence of a neurological disorder. In one embodiment, the response field potentials are analyzed to indicate an imminent neurological event. For example, the response field potentials of the sensed response are used to determine the functional interconnectivity of the brain structure across which the stimuli of the first pulse pattern were delivered. In one embodiment, this is done by taking the ratio of the signals, as previously described, and analyzing the ratio for changes in the signals. Once a likely neurological event is identified, therapy for treating and/or preventing the neurological disorder is delivered to the patient.

Alternatively, the sensed response magnetic fields are analyzed to predict the likelihood of occurrence of a neurological disorder. In one embodiment, the response magnetic fields are analyzed to indicate an imminent neurological event. For example, the response magnetic fields of the sensed response are used to determine the functional interconnectivity of the brain structure across which the stimuli of the first pulse pattern were delivered. In one embodiment, this is done by taking the ratio of the signals, as previously described, and analyzing the ratio for changes in the signals. Once a likely neurological event is identified, therapy for treating and/or preventing the neurological disorder is delivered to the patient.

In one embodiment, when an indication that an epileptic seizure is about to begin, therapy to the patient can include delivering electrical therapy pulses at a high frequency to prevent the occurrence of the seizure. Alternatively, the indication of a seizure could cause medication to be administered to the patient. In one embodiment, the drugs are administered through the use of an automatic implantable drug pump under the control of a microprocessor, where a signal that an imminent seizure is going to occur causes the drug pump to administer the medication.

Figure 2:
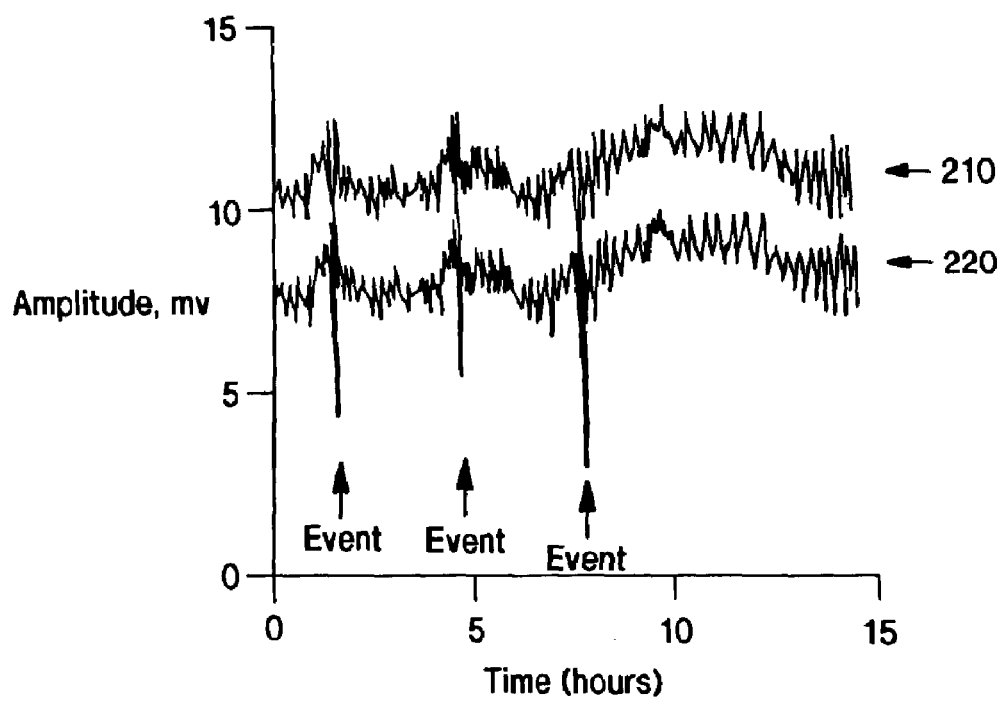
FIG. 2 is a diagrammatic illustration of evoked field potential signals as a function of time according to one embodiment of the present invention.

FIG. 2 is a graph illustrating repetitive field potential responses generated by many repetitions of the stimuli as function of time. In the example shown in FIG. 2, stimuli pairs were repeatedly delivered at their repetition frequency over the course of hours. The response field potentials includes a first signal 210, representative of the response field potentials to the first pulses, and a second signal 220, representative of the response field potentials to the second pulses. In one embodiment, the difference in signal magnitude for the first signal 210 and the second signal 220 is an indicator of the balance between excitation and inhibition of the brain structure where the field potentials are being generated and sensed. In one embodiment, the functional interconnectivity is determined by taking the ratio of the magnitudes of the first and second response field potentials to the first and second pulses, respectively.

Figure 3:
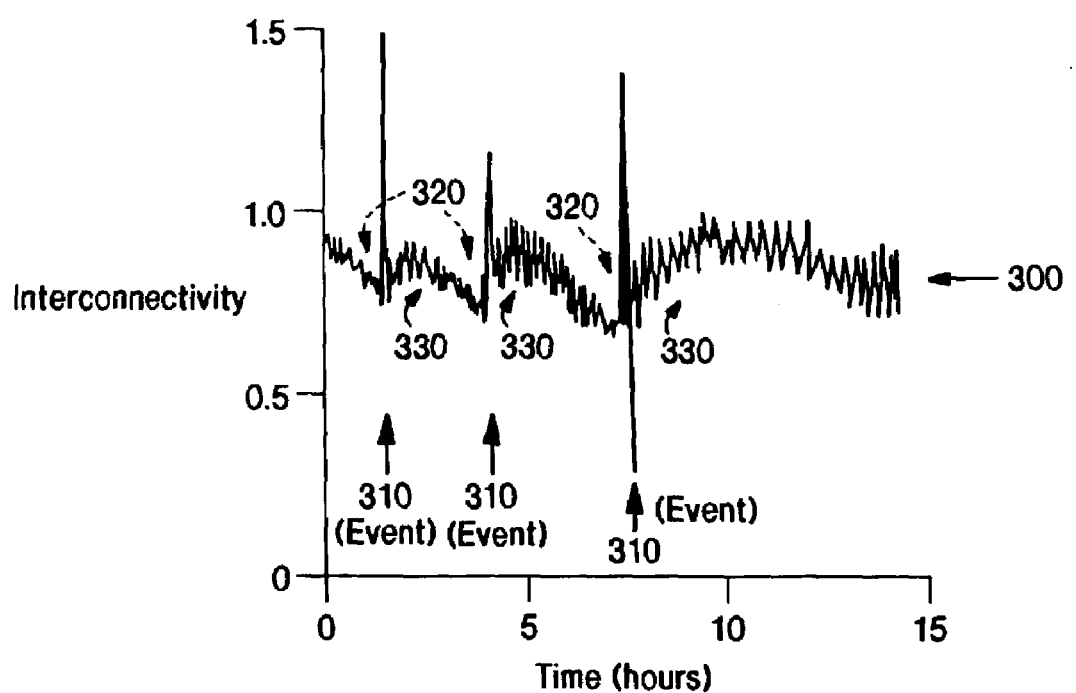
FIG. 3 is a diagrammatic illustration of an indicator of interconnectivity according to one embodiment of the present invention.

FIG. 3 shows an example of an indicator of functional interconnectivity 300 according to the present invention. To arrive at this plot, the ratio is calculated by dividing the field potential maximal amplitudes for the response evoked by the first stimuli and the field potential maximal amplitudes for the response evoked by the second stimuli. FIG. 3 shows these values plotted versus time. FIG. 3 also provides indicators 310 where neurological events (in this case epileptic seizures) occurred over time. As noted, the signals plotted on FIGS. 2 and 3 represent the magnitude of many field potentials evoked by as many sets of stimuli. As discussed for one example, the pulse pattern is repeatedly delivered to the patient, where the pulse pattern has a repetition frequency that has a time that is typically longer than the time to deliver the stimuli of the pulse pattern. Thus, many (e.g., thousands) of response field potentials are represented in FIGS. 2 and 3.

In one embodiment, the functional interconnectivity 300 just prior to the indicator 310 of the neurological event is an important aspect of the present subject matter. As FIG. 3 shows, there is a decrease 320 in the functional interconnectivity 300 just prior to each of the neurological events 310. In one embodiment, this decrease 320 in the functional interconnectivity 300 indicates the likelihood that a neurological event, such as an epileptic seizure, is about to start. As FIG. 3 indicates, the decrease 320 in the functional interconnectivity has a negative slope. In one embodiment, the value of the negative slope increases just prior to the neurological event 310. Predictions as to the onset of an impending neurological event can be based on the detection and analysis of these intervals of functional interconnectivity 300 that display a negative slope.

In one embodiment, when a threshold value of the negative slope is reached, a likely neurological event is indicated. This indicator can be used alone, or in combination with other parameters extracted from the recorded field potentials, to determine that an impending neurological event is likely to occur. For example, in addition to a negative slope, a positive slope, under or overshoot, time to peak, half width of the response, description of the response with an alfa-function, or a series of exponential functions raised to any order might be used in identifying a likely neurological event. In addition, locating the threshold value can also be a self-learning process where the system tries to interact by means of a therapy with certain brain structures. Depending on the number of false positives or false negatives the system may adjust its therapy.

FIG. 3 also indicates that there is a positive slope 330 in the interconnectivity that follows the end of the neurological event 310. This positive slope 330 can be viewed as a resetting of the interconnectivity of the brain structures being monitored. It is believed that delivering therapy during the negative slope 320 will produce this positive slope 330 in the interconnectivity 300. It would, therefore, be possible to maintain a balance between negative and positive slopes in the interconnectivity 300 signal. By maintaining a balanced level of the interconnectivity the onset of a seizure is prevented. Thus, the resetting of the interconnectivity is believed to be an important aspect of preventing the neurological events, such as seizures.

Animal experiments were conducted to test and to provide support for the present invention. In the present example, rats were used as an epileptic model. Rats were made epileptic using an established model of temporal lobe epilepsy (self sustained limbic seizure epilepsy, SSLSE). In this mode, status epilepticus is evoked in the rat after about one hour of tetanic stimulation. Status was then stopped, and the rat was allowed to recover. During recovery, the rat develops temporal lobe epilepsy with spontaneous seizures. This model and the techniques are well tested and published. See Lothman et al., Epilepsie Res., 1989, 3:107–119, and J. Neurophysiol. 1995, 74:2, 829–840.

A set of electrodes was implanted amidst the Schaffer collaterals in the hippocampus of the rat and used for the delivery of electrical pulses. Recording electrodes were implanted in area CA1 in the Stratum Pyramidale (sP) as well as in the Statum Radiatum (sR). Both electrodes measured the field potentials evoked by patterned stimulus pulses delivered by the electrode amidst the Schaffer collaterals. In addition, these electrodes were used to continuously record normal and epileptic brain activity.

Figure 4:
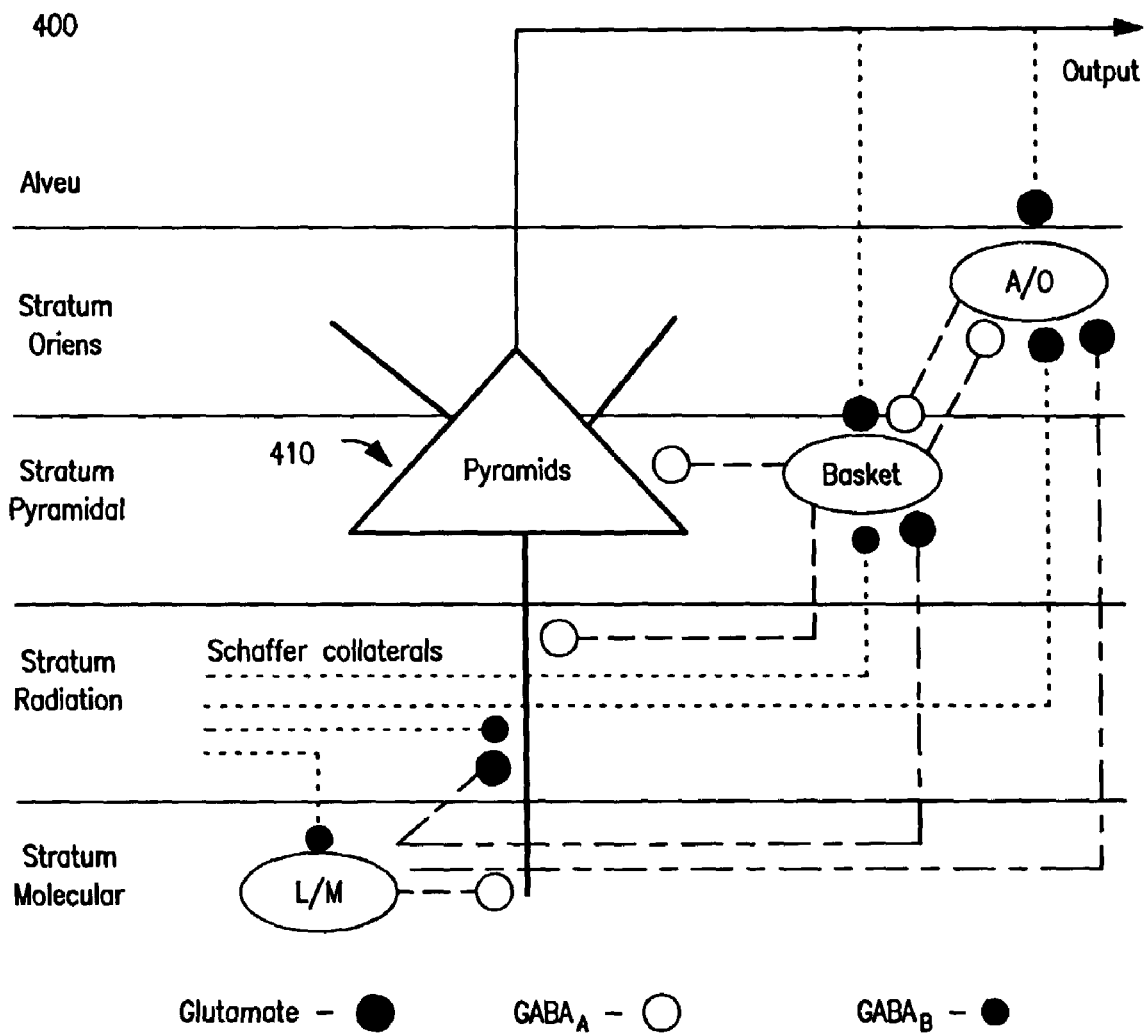
FIG. 4 is a diagrammatic illustration of a cross section of a hippocampus.
Figure 5:
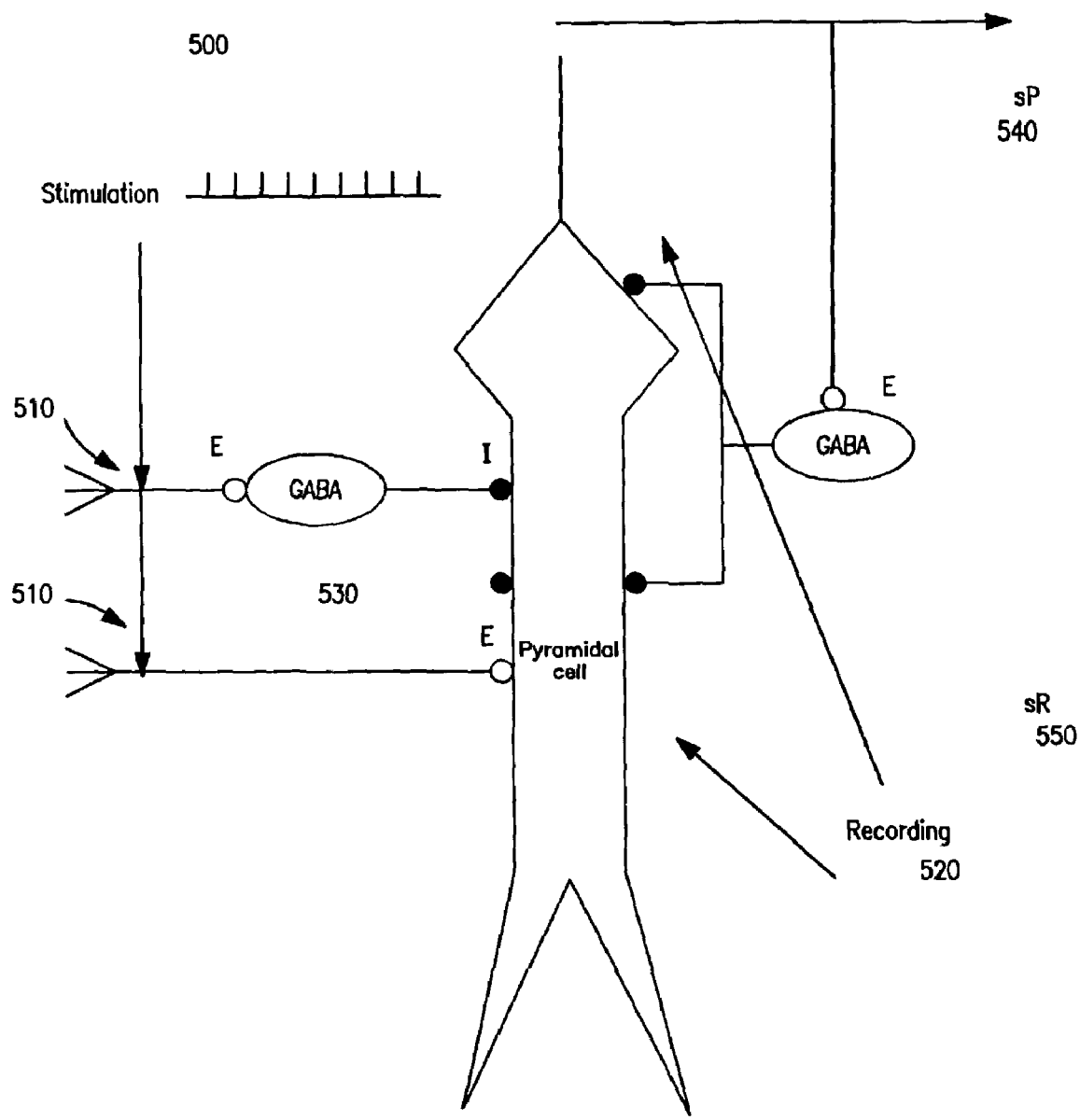
FIG. 5 is a schematic structure of cells within a hippocampus.

FIG. 4 shows a schematic illustration of the hippocampus 400 of the rat and the main structures of the pyramidal cells 410. FIG. 5 shows a schematic structure of a local circuit 500 within the hippocampus of the rat. The local circuit 500 includes stimulation electrodes 510 and recording electrodes 520. During the experiments, the stimulation electrodes 510 were located near the Schaffer collaterals input fibers 530 of the hippocampus. The recording electrodes were positioned in the stratum Pyramidale (sP) 540 and the Stratum Radiatum (sR) 550.

Figure 6:
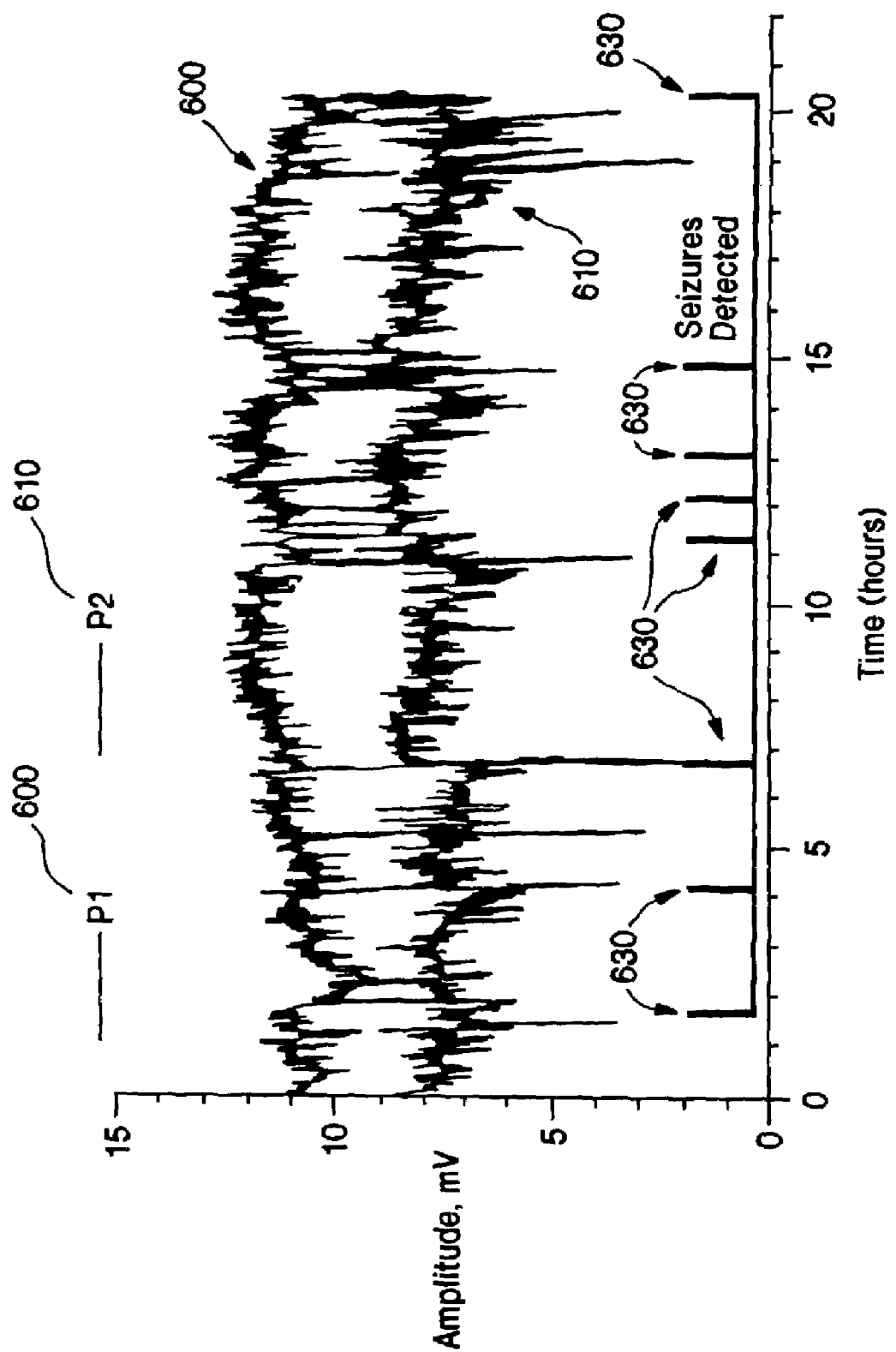
FIG. 6 is a graph illustrating recorded evoked field potential signals as a function of time according to one embodiment of the present invention.

FIG. 6 is a graph illustrating the magnitude of field potential recordings evoked by repeatedly delivered pulse patterns in the rat experiment described above. In this example, the pulse pattern delivered includes pairs of electrical stimuli repeatedly delivered over a 24 hour time interval, where the first and second electrical stimulus of each pair of stimuli were separated by 20 milliseconds, and each pair of stimuli was repeated at a 10 second interval over the 24 hours. The voltage amplitude of each stimulus was in the range of 4 to 10 millivolts and the duration of each stimulus was in the range of 4 to 8 milliseconds. It is noted, however, that the appropriate voltage amplitude, like other parameters of the stimuli, generally will be determined according to the particular brain structure being analyzed for functional interconnectivity.

In FIG. 6, the response field potential signals include a first signal 600 measured at a first position, and a second signal 610 measured at a second position within the rat brain. In the present example, the first signal 600 was recorded in the Stratum Pyramidale (sP) and the second signal 610 was recorded in the Stratum Radiatum (sR). As FIG. 6 shows, the first signal 600 is the magnitude of the response field potentials to the first electrical stimuli and the second signal 610 is the magnitude of the response field potentials to the second electrical stimuli of the repeatedly delivered pulse pattern. Over the 24 hour interval, epileptic seizures 630 were detected visual inspection.

Figure 7:
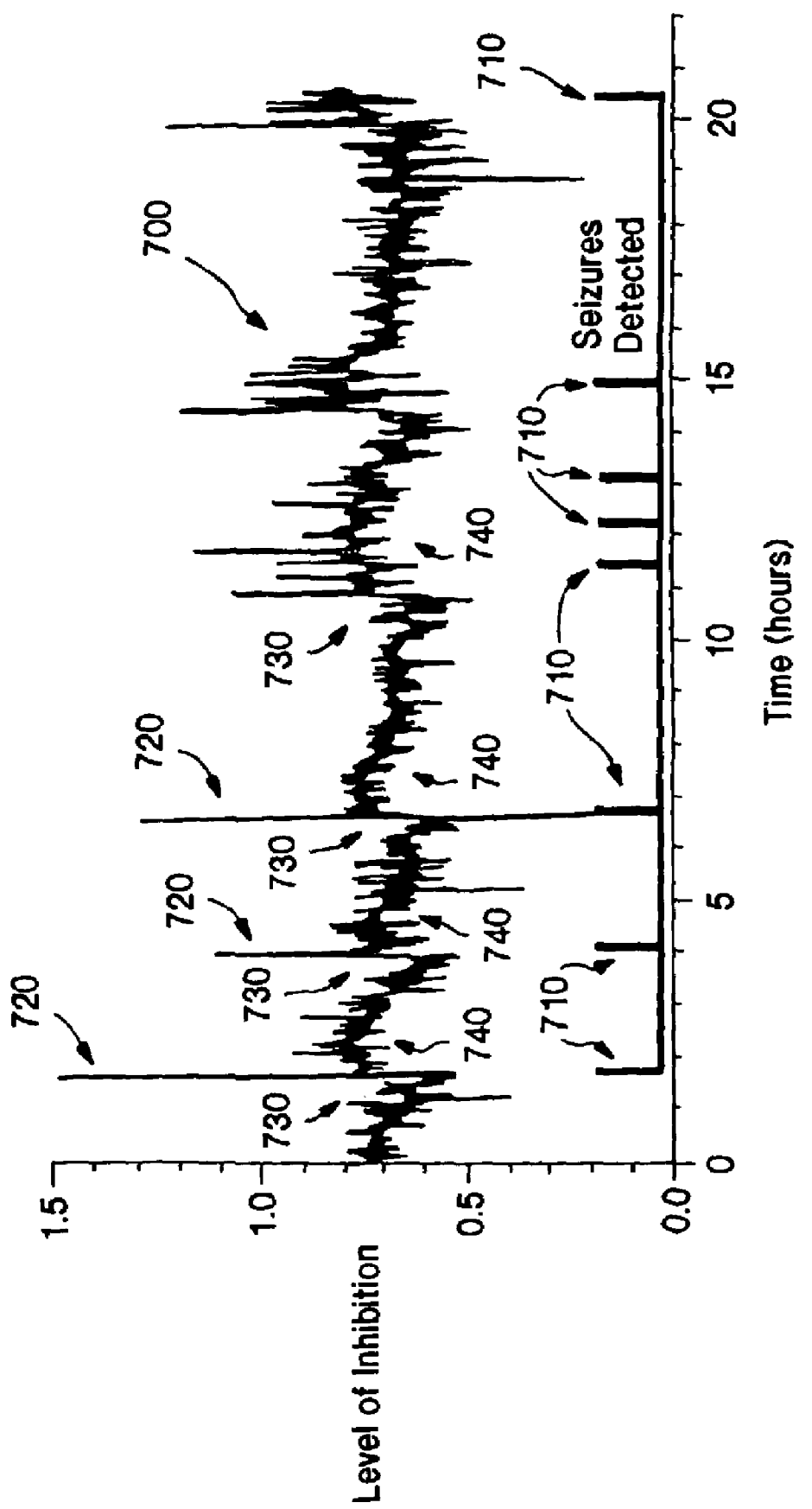
FIG. 7 is a graph illustrating an indicator of interconnectivity, being the ratio of the amplitudes of many evoked field potentials measured in two locations in the brain as function of the time according to one embodiment of the present invention.

FIG. 7 shows one measure of the functional interconnectivity 700 as determined from field potential signals 600 and 610 for the example of FIG. 6. The functional interconnectivity 700 of the sensed field potential signal is determined by taking a ratio of the amplitude of the many field potentials for the first signal 600 to the many field potentials for the second signal 610, as previously discussed. The level of functional interconnectivity 700 calculated in the ratio of field potential values provides for an indication for the likelihood that a neurological event, such as an epileptic seizure 710, is about to start. FIG. 7 also shows decreases 730 in the functional interconnectivity 700 just prior to each of the seizures 710.

In one embodiment, this decrease 730 in the functional interconnectivity 700 indicates the likelihood that a neurological event, such as an epileptic seizure, is about to start. As FIG. 7 indicates, the decrease 730 in the interconnectivity has a negative slope. In one embodiment, this negative slope increases just prior to the epileptic seizure 710. Predictions as to the onset of a likely epileptic seizure 710 can be based on the detection and analysis of these intervals of functional interconnectivity 700 that display a negative slope and, in particular, an abrupt increase in the negative slope.

FIG. 7 also shows a positive slope 740 in the functional interconnectivity that follows the end of the neurological event 710. This positive slope 740 can be viewed as a resetting of the interconnectivity of the brain structures being monitored. It is believed that delivering therapy during the negative slope 730 will produce this positive slope 740 in the functional interconnectivity 700. It would, therefore, be possible to maintain a balance between negative and positive slopes in the functional interconnectivity 700 signal. By maintaining a balanced level of the interconnectivity the onset of a seizure is prevented. Thus, the resetting of the interconnectivity is believed to be an important aspect of preventing the neurological events, such as seizures.

Figure 8:
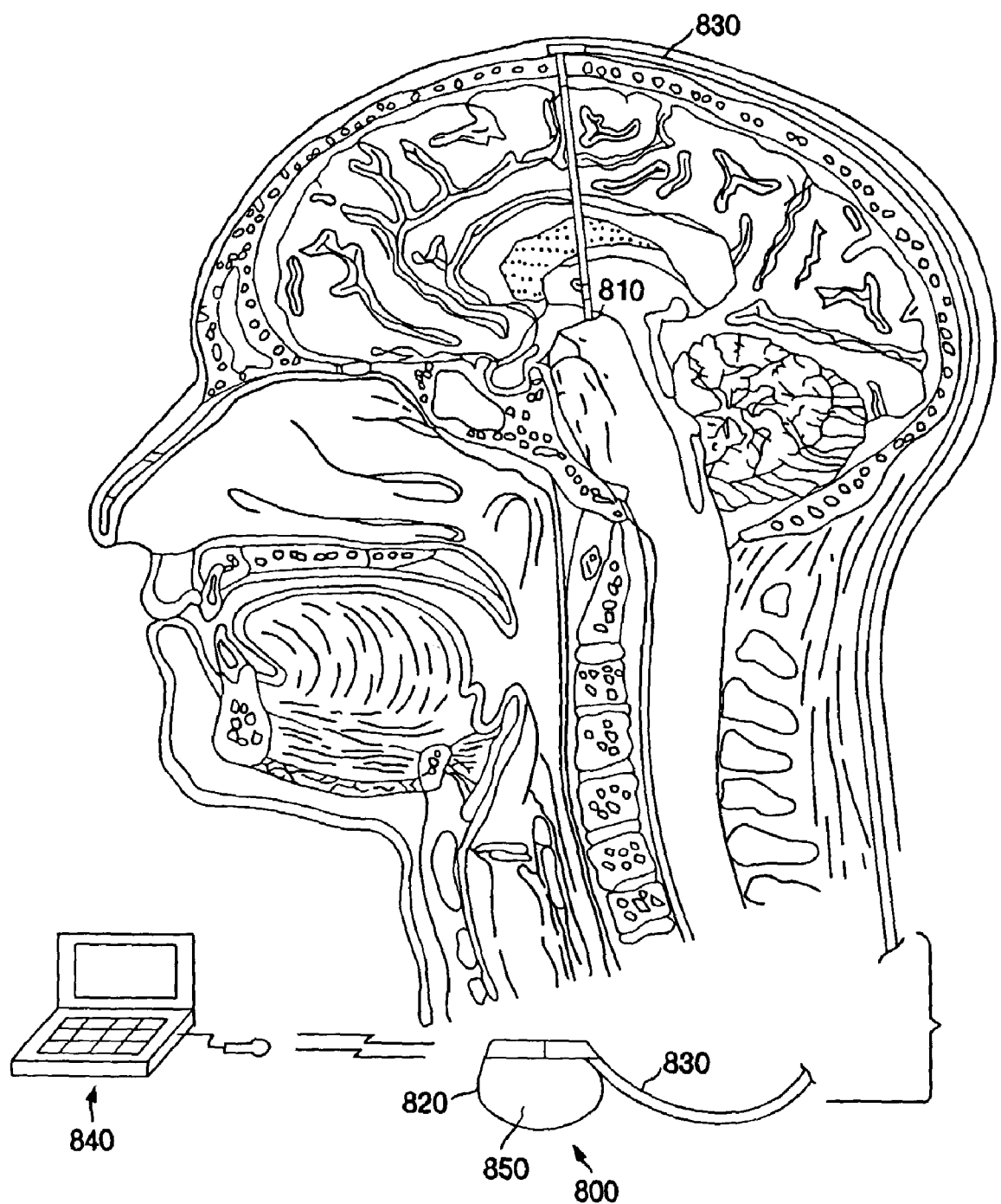
FIG. 8 is diagram of a system according to one embodiment of the present invention.

FIG. 8 shows one embodiment of a system 800 according to the present invention. In one embodiment, portions of system 800 can be implanted below the skin of a patient. The system includes generally one or more electrodes 810 implantable in a structure of a brain. Electrodes 810 can serve to deliver electrical stimuli to the structure of the brain under the control of the signal processor/generator 820. The signal processor/generator 820 also use electrodes 810 to receive response field potentials to the electrical stimuli delivered to the brain. In an alternative embodiment, additional electrodes are implanted in the brain to sense the response field potentials to the electrical stimulation.

Electrodes 810 can be implanted in any one or more structures of the brain, as previously described. In the example shown in FIG. 8, electrodes 810 are coupled to the signal processor/generator 820 through lead 830. Electrodes 810 can take the form of a device capable of detecting nerve cell or axon activity. In one embodiment, electrodes 810 are located deep in the brain parachyma in any one or more structures of the brain, as previously described. Alternatively, the electrodes may be inserted into the seizure focus or part of the central nervous system where seizures begin. A medical device programmer/controller 840 is also used to communicate and program the signal processor/generator 820. In one embodiment, the medical device programmer/controller 840 transmits and receives data from the signal processor/generator 820 communicate with the implanted pulse generator through a telemetry link. Such telemetric systems may use, for example, radio frequency, ultrasound, infrared or other like communication means.

In one embodiment, the one or more electrodes 810 on lead 830 serve not only to deliver the electrical stimuli, but also to receive the response field potentials. Alternatively, additional electrodes on one or more additional leads can be used to either deliver electrical stimuli and/or sense the response field potentials. Each electrode 810 is individually connected to the signal processor/generator 820 through a wire conductor in lead 830. Depending upon the situation, one or more stimulation/sensing leads with any number of electrodes may be used. For example, lead model 3387 DBS™ sold by Medtronic, Inc. of Minneapolis, Minn. may be used. Additional useful sensing and stimulation lead models include models 3389 DBS™ and 3388 DBS™, also sold by Medtronic, Inc.

The signal processor/generator 820 includes an electrical pulse generator and a signal analyzer encased in an implantable housing 850. In one embodiment, the implantable housing is a hermetically sealed housing. The electrical pulse generator produces and delivers electrical pulses to electrodes 810. The signal analyzer processes signals received by electrodes 810 and predicts the occurrence of a neurological disorder.

Figure 9:
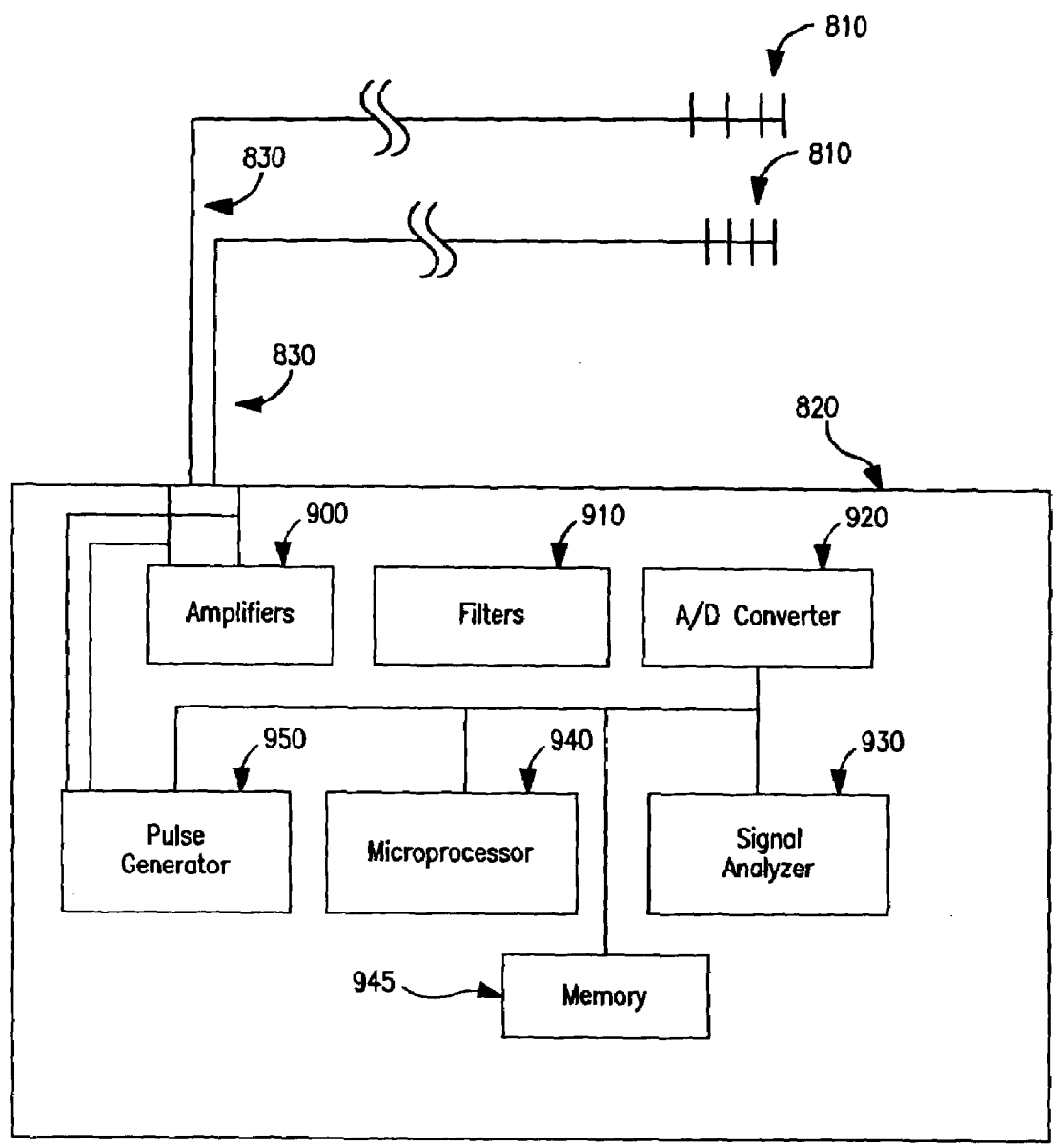
FIG. 9 is a block diagram of one embodiment of the system of FIG. 8 according to the present invention.

FIG. 9 is a block diagram depicting signal processor/generator 820 of the present invention in greater detail. Response field potentials sensed with one or more of electrodes 810 are amplified and filtered by amplifier 900 and filter 910, respectively. The response field potential signals are then converted to a digital representation by analog to digital converter 920. The response field potentials may then be further processed by a signal analyzer 930 or may be input to a microprocessor 940 for processing.

In one embodiment, the signal analyzer 930 is used to process response field potentials received by one or more of electrodes 810 and to predict the occurrence of a neurological disorder based on the sensed responses. Alternatively, the microprocessor 940 could be used for processing the response field potentials received by one or more of electrodes 810 and predicting the occurrence of the neurological disorder based on the sensed potentials. In one embodiment, processing the field potentials and predicting the occurrence of the neurological disorder is accomplished through the use of an algorithm stored in a memory 945. The algorithm can be embodied as program code retrieved from memory 945 and executed by microprocessor 940.

Microprocessor 940 is also coupled to an electrical pulse generator 950. The electrical pulse generator 950 delivers electrical stimuli to one or more of the electrodes 810 implanted in the structure of the brain under the control of microprocessor 940. The electrical pulse generator 950 is used to deliver stimuli having the pulse pattern, as previously described. For example, the pulse pattern can include pairs of a first stimulus and a second stimulus that are repeatedly delivered to the patient.

The signal analyzer 930 is then used to measures changes in the responses to the second stimuli as compared to the responses to the first stimuli, as previously discussed. In one embodiment, the signal analyzer 930 measures the field potential of the responses received from a first location and a section location within the brain. The Signal analyzer 930 determines the level of functional interconnectivity from a ratio of the response field potentials measured at the first and second locations, as previously described. The signal analyzer 930 indicates a likely epileptic event when the level of interconnectivity displays, for example, a negative slope. In addition to the negative slope, signal analyzer 930 indicates the imminent epileptic event when the negative slope, for example, exceeds a predetermined threshold value.

When a likely neurological episode has been identified, microprocessor 940 controls the delivery of therapy to the patient. In one embodiment, the therapy includes the use of electrical pulse generator 950 to deliver therapy in the form of electrical pulses for the neurological disorder when the change in the response field potentials exceeds a threshold value. In one embodiment, locating the threshold value can be a self-learning process where the system tries to interact by means of a therapy with certain brain structures.

The therapy pulses of electrical energy can be delivered to electrodes 810 and/or additional electrodes implanted in the brain. In one embodiment, the therapy pulses are delivered at a high frequency to prevent the occurrence of the neurological disorder. Other therapy pulse patterns are also possible. Depending on the number of false positives or false negatives the system may adjust therapy. Additional therapy techniques and processes could be added to the signal processor/generator for treating the patient. For example, therapies under the control of the signal processor/generator could include drug pumps for delivering anti-seizure medication to the patient.

At the time the present invention is implanted within the patient, the clinician may program certain key parameters into the memory of the implanted device or may do so via telemetry. These parameters may be updated subsequently as needed. Alternatively, the clinician may elect to use default values. The clinician ordinarily will program the range of values for pulse width, magnitude and frequency. The clinician can adjust the parameters of the electrical pulses via telemetry with a medical device programmer. In order to assess the interconnection of the brain, the sensed signals can be stored in memory 945 over time, and retrieved by telemetry for assessment by the physician. The physician can use the stored data to reset therapy or monitoring characteristics in system 820.

The preceding specific embodiments are illustrative for the practice of the invention. It is to be understood, therefore, that other expedients known to those skilled in the art or disclosed herein, may be employed without departing from the invention or the scope of the appended claims. For example, the present invention is not limited to predicting the onset of an epileptic seizure. The present invention is also not limited to predicting the onset of a neurological event per se, but may find further application as a predictor of migraine headaches, Parkinson's disease, schizophrenia, depression, mania, or other neurological disorders where changes in the balance of the excitatory or inhibitory influences on the brain cells may provide indications of an impending pathological event. The present invention further includes within its scope methods of making and using systems and/or apparatus for carrying out the methods described hereinabove.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention further includes within its scope the methods of making and using the systems described above. These methods are not limited to the specific examples described above, but may be adapted to meet the needs of a particular patient. These and other embodiments are within the scope of the following claims.

The invention claimed is:

1. A method comprising:
    delivering electrical stimuli having a pulse pattern to a structure of a brain, wherein delivering stimuli having the pulse pattern includes delivering a first stimulus and a second stimulus to the structure;
    sensing response field potentials evoked by the stimuli delivered to the structure wherein the sensed response field potentials are represented in a sensed signal and wherein sensing response field potentials includes measuring a change in a response field potential to the second stimulus as compared to the response field potential to the first stimulus; and
    storing the sensed signal in memory.

2. The method of claim 1, wherein delivering the first stimulus and the second stimulus includes delaying delivery of the second stimulus relative the first stimulus by a time interval of 5 to 2000 milliseconds.

3. The method of claim 1, wherein delivering the first stimulus and the second stimulus includes delaying delivery of the second stimulus relative the first stimulus by a time interval of 5 to 1000 milliseconds.

4. The method of claim 1, wherein delivering the first stimulus and the second stimulus includes delaying delivery of the second stimulus relative the first stimulus by a time interval of 100 to 2000 milliseconds.

5. The method of claim 1, wherein delivering the first stimulus and the second stimulus includes delaying delivery of the second stimulus relative the first stimulus by a time interval of 100 to 1000 milliseconds.

6. The method of claim 1, including repeating the delivery of the first pulse pattern at a repetition frequency of 1 second to 30 minutes.

7. The method of claim 1, including repeating the delivery of the first pulse pattern at a repetition frequency of 1 minute to 30 minutes.

8. The method of claim 1, including repeating the delivery of the first pulse pattern at a repetition frequency of 1 second to 10 minutes.

9. The method of claim 1, including repeating the delivery of the first pulse pattern at a repetition frequency of 1 minute to 10 minutes.

10. The method of claim 1, including repeating the delivery of the first pulse pattern at a repetition frequency of 1 second to 10 minute.

11. A method comprising:
    delivering electrical stimuli to a structure of a brain wherein delivering stimuli to the structure includes delivering the stimuli to an afferent fiber or efferent fiber system in the structure of the brain;
    sensing response field potentials evoked by the stimuli delivered to the structure wherein the sensed response field potentials are represented in a sensed signal; and
    storing the sensed signal in memory.

12. A method comprising:
    implanting one or more electrodes in a structure of a brain wherein implanting one or more electrodes includes implanting a lead that includes the one or more electrodes in the structure of the brain;
    delivering electrical stimuli having a first pulse pattern to the structure through the electrodes, wherein the first pulse pattern includes pairs of two or more electrical stimuli;
    sensing response field potentials evoked by the stimuli delivered to the structure wherein the sensed response field potentials are represented in a sensed signal; and
    storing the sensed signal in memory.

13. A method comprising:
implanting one or more electrodes in a structure of a brain wherein implanting one or more electrodes includes implanting a lead that includes the one or more electrodes in the structure of the brain;
delivering electrical stimuli having a first pulse pattern to the structure through the electrodes, wherein delivering stimuli having the first pulse pattern includes delivering a first stimulus and a second stimulus to the structure;
sensing response field potentials evoked by the stimuli delivered to the structure wherein the sensed response field potentials are represented in a sensed signal; and
storing the sensed signal in memory, wherein sensing response field potentials includes measuring a change in a response field potential to the second pulse as compared to the response field potential to the first pulse.

14. The method of claim 13, wherein delivering the first stimulus and the second stimulus includes delaying delivery of the second stimulus relative the first stimulus by a time interval of 5 to 2000 milliseconds.

15. The method of claim 13, wherein delivering the first stimulus and the second stimulus includes delaying delivery of the second stimulus relative the first stimulus by a time interval of 5 to 1000 mIlliseconds.

16. The method of claim 13, wherein delivering the first stimulus and the second stimulus includes delaying delivery of the second stimulus relative the first stimulus by a time interval of 100 to 2000 milliseconds.

17. The method of claim 13, wherein delivering the first stimulus and the second stimulus includes delaying delivery of the second stimulus relative the first stimulus by a time interval of 100 to 1000 milliseconds.

18. The method of claim 13, including repeating the delivery of the first pulse pattern at a repetition frequency of 1 second to 30 minutes.

19. The method of claim 13, including repeating the delivery of the first pulse pattern at a repetition frequency of 1 minute to 30 minutes.

20. The method of claim 13, including repeating the delivery of the first pulse pattern at a repetition frequency of 1 second to 10 minutes.

21. The method of claim 13, including repeating the delivery of the first pulse pattern at a repetition frequency of 1 minute to 10 minutes.

22. The method of claim 13, including repeating the delivery of the first pulse pattern at a repetition frequency of 1 second to 1 minute.

23. A method comprising:
implanting one or more electrodes in a structure of a brain wherein implanting one or more electrodes includes implanting a lead that includes the one or more electrodes in the structure of the brain;
delivering electrical stimuli to the structure through the electrodes, wherein delivering stimuli to the structure includes delivering the stimuli to an afferent fiber or an efferent fiber system in the structure of the brain;
sensing response field potentials evoked by the stimuli delivered to the structure wherein the sensed response field potentials are presented in a sensed signal; and
storing the sensed signal in memory.

24. A system comprising:
one or more electrodes implantable in a structure of a brain;
a signal processor/generator coupled to the electrodes, wherein the signal generator includes:
an electrical pulse generator to deliver electrical stimuli to the brain via the electrodes implanted in the structure of the brain;
a memory means for receiving from the electrodes a sensed signal representing the response field potentials to the electrical stimuli, the memory to store the sensed signal; and
wherein the electrical pulse generator repeatedly delivers the first pulse pattern at a repetition frequency of 1 second to 30 minutes.

25. A system comprising:
one or more electrodes implantable in a structure of a brain;
a signal processor/generator coupled to the electrodes, wherein the signal generator includes:
an electrical pulse generator to deliver electrical stimuli to the brain via the electrodes implanted in the structure of the brain;
a memory means for receiving from the electrodes a sensed signal representing the response field potentials to the electrical stimuli, the memory to store the sensed signal; and
wherein the electrical pulse generator repeatedly delivers the first pulse pattern at a repetition frequency of 1 minute to 10 minutes.

26. A system comprising:
means for delivering electrical stimuli to a structure of a brain including means for delivering stimuli having a pulse pattern to the structure;
means for sensing response field potentials evoked by the stimuli delivered to the structure;
means for staring the sensed response field potentials; and
wherein the means for delivering stimuli having the pulse pattern includes means for delivering a first stimulus and a second stimulus to the structure, and the means for sensing response field potentials includes means for measuring a change in a response field potential to the second stimulus as compared to the response field potential to the first stimulus.

27. A system comprising:
means for implanting one or more electrodes in a structure of a brain;
means for delivering electrical stimuli to the structure through the electrodes wherein the means for delivering stimuli includes means for delivering stimuli having a first pulse pattern;
means for sensing response field potentials evoked by the stimuli delivered to the structure;
means for storing the response field potentials; and
wherein the means for delivering stimuli having the first pulse pattern includes means for delivering a first stimulus and a second stimulus to the structure, and the means for sensing response field potentials includes means for measuring a change in a response field potential to the second pulse as compared to the response field potential to the first pulse.

28. A system comprising:
one or more electrode means implantable in a structure of a brain;
a signal processor/generator means coupled to the electrode means, wherein the signal generator means includes:
an electrical pulse generator means to deliver electrical stimuli having a first pulse pattern to the brain via the electrode means implanted in the structure of the brain;

a storage means to receive via the electrode means response field potentials to the electrical stimuli delivered with the electrical pulse generator means, where the storage means receives response field potentials through the electrode means and stores the response field potentials; and wherein the electrical pulse generator means delivers the first pulse pattern that includes a first stimulus and a second stimulus, and the signal processor means measures changes in the response field potentials to the second stimulus as compared to the response field potentials to the first stimulus.

29. A method comprising:

delivering electrical stimuli to a structure of a brain;

sensing response field potentials evoked by the stimuli delivered to the structure wherein the sensed response field potentials are represented in a sensed signal;

analyzing the sensed response field potentials to predict the likelihood of occurrence of a neurological disorder; and storing the sensed signal in memory.

30. The method of claim 29, wherein the storing the sensed signal comprises storing a raw sensed signal.

31. The method of claim 29, wherein delivering stimuli to the structure includes delivering stimuli having a pulse pattern to the structure.

32. The method of claim 31, wherein delivering stimuli having the pulse pattern includes delivering a first stimulus and a second stimulus to the structure, and sensing response field potentials includes measuring a change in a response field potential to the second stimulus as compared to the response field potential to the first stimulus.

33. The method of claim 32, wherein sensing response field potentials include sensing the response field potentials from a first location and a section location within the brain, and wherein measuring the change includes:

measuring a field potential evoked by the first stimulus and the field potential evoked by the second stimulus at the first and second location; and determining a level of functional interconnectivity from a ratio of the response field potentials measured at the first and second locations.

34. The method of claim 33, wherein analyzing the sensed response field potentials includes indicating a likely epileptic event when the level of functional interconnectivity exceeds a predetermined threshold value.

35. The method of claim 33, wherein analyzing the sensed response field potentials includes indicating a likely epileptic event when the level of functional interconnectivity has a negative slope.

36. The method of claim 32, including delivering a therapy forte neurological disorder when the change in the response field potentials exceeds a threshold value.

37. The method of claim 36, wherein delivering the therapy includes delivering therapy pulses at a high frequency to prevent the occurrence of the neurological disorder.

38. The method of claim 29, wherein analyzing the sensed response field potentials includes analyzing the sensed response field potentials pulses to predict the likelihood of occurrence of an epileptic seizure.

39. The method of claim 29, wherein delivering stimuli to the structure includes delivering a predetermined number of stimuli to the structure.

40. The method of claim 29, wherein delivering stimuli to the structure includes delivering the stimuli to an afferent fiber or efferent fiber system in the structure of the brain.

41. A method comprising:

implanting one or more electrodes in a structure of a brain;

delivering electrical stimuli to the structure through the electrodes;

sensing response field potentials evoked by the stimuli delivered to the structure;

processing the response field potentials to predict the likelihood of occurrence of a neurological disorder based on the sensed response field potentials; and storing the sensed response field potentials in memory.

42. The method of claim 41, wherein implanting the electrodes includes positioning each of the electrodes in communication with a predetermined site in a brain.

43. The method of claim 42, wherein positioning includes selecting the predetermined site from the group consisting of the sub thalamic nucleus, the hippocampus, the medial thalanus and the temporal lobe.

44. The method of claim 41, wherein implanting one or more electrodes includes implanting a lead that includes the one or more electrodes in the structure of the brain.

45. The method of claim 41, wherein sensing response field potentials includes sensing response field potentials with the one or more electrodes.

46. The method of claim 41, wherein sensing response field potentials includes sensing field potentials generated in the brain structure.

47. The method of claim 41, where delivering stimuli includes delivering stimuli having a first pulse pattern.

48. The method of claim 47, wherein the first pulse pattern includes pairs of two or more electrical stimuli.

49. The method of claim 47 wherein delivering stimuli having the first pulse pattern includes delivering a first stimulus and a second stimulus to the structure, and sensing response field potentials includes measuring a change in a response field potential to the second pulse as compared to the response field potential to the first pulse.

50. The method of claim 49, including repeating the delivery of the first pulse pattern at a repetition frequency of 1 minute to 30 minutes.

51. The method of claim 49, including repeating the delivery of the first pulse pattern at a repetition frequency of 1 second to 10 minutes.

52. The method of claim 49, wherein sensing response field potentials include sensing the response field potentials from a first location and a section location within the brain; and wherein measuring the change includes:

measuring a field potential evoked by the first stimulus and the field potential evoked by the second stimulus at the first and second location; and determining a level of functional interconnectivity from a ratio of the response field potentials measured at the first and second locations.

53. The method of claim 52, wherein processing the response field potentials includes indicating a likely epileptic event when the level of functional interconnectivity exceeds a predetermined threshold value.

54. The method of claim 52, wherein processing the response field potentials includes indicating a likely epileptic event when the level of functional interconnectivity has a negative slope.

55. The method of claim 49, including delivering a therapy for the neurological disorder when the change in the response field potential exceeds a threshold value.

56. The method of claim 55, wherein delivering the therapy includes delivering therapy pulses at a high frequency to prevent the occurrence of the neurological disorder.

57. The method of claim 41, wherein processing the response field potentials includes identifying the occurrence of an epileptic seizure based on the sensed response field potentials.

58. The method of claim 41, wherein delivering stimuli to the structure includes delivering the stimuli to an afferent fiber or an efferent fiber system in the structure of the brain.

59. A system comprising:
one or more electrodes implantable in a structure of a brain;
a signal processor/generator coupled to the electrodes, wherein the signal generator includes:
an electrical pulse generator to deliver electrical stimuli to the brain via the electrodes implanted in the structure of the brain;
a signal analyzer to receive via the electrodes response field potentials to the electrical stimuli delivered with the electrical pulse generator, where the signal analyzer receives response field potentials through the electrodes and predicts the likelihood of the occurrence of a neurological disorder based on the sensed response field potentials; and
a memory to receive from the electrodes a sensed signal representing the response field potentials to the electrical stimuli, the memory to store the sensed signal.

60. The system of claim 59 wherein the sensed signal stored in memory comprises a raw sensed signal.

61. The system of claim 59, wherein the electrical pulse generator delivers stimuli having a first pulse pattern.

62. The system of claim 61, wherein the electrical pulse generator delivers pairs of two or more electrical stimuli.

63. The system of claim 61, wherein the electrical pulse generator delivers the first pulse pattern that includes a first stimulus and a second stimulus, and the signal analyzer measures changes in the response field potentials to the second pulse as compared to the response field potentials to the first pulse.

64. The system of claim 63, wherein the signal analyzer measures the field potential of the response field potentials received from a first location and a section location within the brain, and determines a level of functional interconnectivity from a ratio of the response field potentials measured at the first and second locations.

65. The system of claim 64, wherein the signal analyzer indicates a likely epileptic event when the level of functional interconnectivity exceeds a predetermined threshold value.

66. The system of claim 64, wherein the signal analyzer indicates a likely epileptic event when the level of functional interconnectivity has a negative slope.

67. The system of claim 63, wherein the electrical pulse generator delivers a therapy for the neurological disorder when the change in the response field potentials exceeds a threshold value.

68. The system of claim 67, wherein the electrical pulse generator delivers the therapy pulses at a high frequency to prevent the occurrence of the neurological disorder.

69. The system of claim 59, wherein the signal analyzer indicates the likelihood of an occurrence of an epileptic seizure based on the response field potentials.

70. The system of claim 59, wherein the system includes a lead having the one or more electrodes.

71. The system of claim 59, wherein the signal processor/generator is encased in an implantable housing.

72. A system comprising:
means for delivering electrical stimuli to a structure of a brain;
means for sensing response field potentials evoked by the stimuli delivered to the structure;
means for analyzing the sensed response field potentials to predict the likelihood of occurrence of a neurological disorder; and
means for storing the sensed response field potentials.

73. The system of claim 72 wherein the means for storing sensed response field potentials comprises means for storing raw sensed response field potentials.

74. The system of claim 72, wherein the means for delivering stimuli to the structure includes means for delivering stimuli having a pulse pattern to the structure.

75. The system of claim 74, wherein the means for delivering stimuli having the pulse pattern includes means for delivering a first stimulus and a second stimulus to the structure, and the means for sensing response field potentials includes means for measuring a change in a response field potential to the second stimulus as compared to the response field potential to the first stimulus.

76. The system of claim 75, wherein the means for sensing response field potentials include means for sensing the response field potentials from a first location and a section location within the brain, and wherein the means for measuring the change includes:
means for measuring a field potential evoked by the first stimulus and the field potential evoked by the second stimulus at the tint and second location; and
means for determining a level of functional interconnectivity from a ratio of the response field potentials measured at the first and second locations.

77. The system of claim 76, wherein the means for analyzing the sensed response field potentials includes means for indicating a likely epileptic event when the level of functional interconnectivity exceeds predetermined threshold value.

78. The system of claim 76, wherein the means for analyzing the sensed response field potentials includes means for indicating a likely epileptic event when the level of functional interconnectivity has a negative slope.

79. The system of claim 75, including means for delivering a therapy for the neurological disorder when the change in the response field potentials exceeds a threshold value.

80. The system of claim 72, wherein the means for analyzing the sensed response field potentials includes means for analyzing the sensed response field potentials pulses to predict the likelihood of occurrence of an epileptic seizure.

81. A system comprising:
means for implanting one or more electrodes in a structure of a brain;
means for delivering electrical stimuli to the structure through the electrodes;
means for sensing response field potentials evoked by the stimuli delivered to the structure;
means far processing the response field potentials to predict the likelihood of occurrence of a neurological disorder based on the sensed response field potentials; and
means for storing the response field potentials.

82. The system of claim 81 wherein the means for storing the response field potentials comprises means for storing raw response field potentials.

83. The system of claim 81, wherein means for implanting one or more electrodes includes means for implanting a lead that includes the one or more electrodes in the structure of the brain.

84. The system of claim 81, where the means for delivering stimuli includes means for delivering stimuli having a first pulse pattern.

85. The system of claim 84, wherein the means for delivering stimuli having the first pulse pattern includes means for delivering a first stimulus and a second stimulus to the structure, and the means for sensing response field potentials includes means for measuring a change in a response field potential to the second pulse as compared to the response field potential to the first pulse.

86. The system of claim 85, wherein the means for sensing response field potentials include means for sensing the response field potentials from a first location and a section location within the brain; and wherein the means for measuring the change includes:
  means for measuring a field potential evoked by the first stimulus and the field potential evoked by the second stimulus at the first and second location; and
  means for determining a level of functional interconnectivity from a ratio of the response field potentials measured at the first and second locations.

87. The system of claim 86, wherein the means for processing the response field potentials includes means for indicating a likely epileptic event when the level of functional interconnectivity exceeds a predetermined threshold value.

88. The system of claim 86, wherein the means for processing the response field potentials includes means for indicating a likely epileptic event when the level of functional interconnectivity has a negative slope.

89. The system of claim 85, including means for delivering a therapy for the neurological disorder when the change in die response field potential exceeds a threshold value.

90. The system of claim 81, wherein the means for processing the response field potentials includes means for identifying the occurrence of an epileptic seizure based on the sensed response field potentials.

91. A system comprising:
  one or more electrode means implantable in a structure of a brain;
  a signal processor/generator means coupled to the electrode means, wherein the signal generator means includes:
    an electrical pulse generator means to deliver electrical stimuli to the brain via the electrode means implanted in the structure of the brain;
    a signal analyzer means to receive via the electrode means response field potentials to the electrical stimuli delivered with the electrical pulse generator means, where the signal analyzer means receives response field potentials through the electrode means and predicts the likelihood of the occurrence of a neurological disorder based on the sensed response field potentials; and
    a storage means to receive via the electrode means response field potentials to the electrical stimuli delivered with the electrical pulse generator means, where the storage means receives response field potentials trough the electrode means and stores the response field potentials.

92. The system of claim 91 wherein the storage means stores raw response field potentials.

93. The system of claim 91, wherein the electrical pulse generator means delivers stimuli having a first pulse pattern.

94. The system of claim 93, wherein the electrical pulse generator means delivers the first pulse pattern that includes a first stimulus and a second stimulus, and the signal analyzer means measures changes in the response field potentials to the second pulse as compared to the response field potentials to the first pulse.

95. The system of claim 94, wherein the signal analyzer means measures the field potential of the response field potentials received from a first location and a section location within the brain, and determines a level of functional interconnectivity from a ratio of the response field potentials measured at the first and second locations.

96. The system of claim 95, wherein the signal analyzer means indicates a likely epileptic event when the level of functional interconnectivity exceeds a predetermined threshold value.

97. The system of claim 95, wherein the signal analyzer means indicates a likely epileptic event when the level of functional interconnectivity has a negative slope.

98. The system of claim 94, wherein the electrical pulse generator means delivers a therapy for the neurological disorder when the change in the response field potentials exceeds a threshold value.

99. The system of claim 91, wherein the signal analyzer means indicates the likelihood of an occurrence of an epileptic seizure based on the response field potentials.

100. The system of claim 91, wherein the system includes lead means having the one or more electrodes.

101. The system of claim 91, wherein the signal processor/generator means is encased in an implantable housing means.

* * * * *

UNITED STATES PATENT AND TRADEMARK OFFICE
CERTIFICATE OF CORRECTION

| | | |
|---|---|---|
| PATENT NO. | : 7,006,872 B2 | Page 1 of 1 |
| APPLICATION NO. | : 10/388926 | |
| DATED | : February 28, 2006 | |
| INVENTOR(S) | : Gielen et al. | |

It is certified that error appears in the above-identified patent and that said Letters Patent is hereby corrected as shown below:

Col. 16, Line 45: "second to 10 minute" should be---second to 1 minute---

Col. 17, Line 61: "potentials are presented" should be—potentials are represented—

Col. 18, Line 32: "means for staring" should be—means for storing—

Col. 19, Line 52: "forte" should be —for the—

Col. 23, Line 37: "change in die" should be---change in the---

Col. 24, Line 13: "trough the" should be---through the---

Signed and Sealed this

Eighth Day of August, 2006

JON W. DUDAS
*Director of the United States Patent and Trademark Office*